(12) United States Patent
Tanaka et al.

(10) Patent No.: US 11,299,826 B2
(45) Date of Patent: Apr. 12, 2022

(54) TUBULAR FABRIC AND BASE MATERIAL FOR MEDICAL USE USING SAME

(71) Applicant: Toray Industries, Inc., Tokyo (JP)

(72) Inventors: Nobuaki Tanaka, Osaka (JP); Satoshi Yamada, Otsu (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 17/049,144

(22) PCT Filed: Apr. 12, 2019

(86) PCT No.: PCT/JP2019/015929
§ 371 (c)(1),
(2) Date: Oct. 20, 2020

(87) PCT Pub. No.: WO2019/208262
PCT Pub. Date: Oct. 31, 2019

(65) Prior Publication Data
US 2021/0238774 A1   Aug. 5, 2021

(30) Foreign Application Priority Data

Apr. 26, 2018   (JP) .............................. JP2018-085164

(51) Int. Cl.
*D03D 3/02*       (2006.01)
*D03D 11/02*      (2006.01)
(Continued)

(52) U.S. Cl.
CPC .................. *D03D 3/02* (2013.01); *D03D 1/00* (2013.01); *D03D 11/02* (2013.01); *A61F 2/06* (2013.01)

(58) Field of Classification Search
CPC . D03D 3/02; D03D 1/00; D03D 11/02; D03D 13/008; D03D 15/283; D03D 11/00; A61F 2/06; D10B 2509/06; D10B 2331/04
See application file for complete search history.

(56) References Cited

U.S. PATENT DOCUMENTS 3,350,488 A * 10/1967 Breen ...................... D01D 5/28
264/172.17
3,531,368 A *  9/1970 Aizawa ................... D01D 5/36
428/374
(Continued)

FOREIGN PATENT DOCUMENTS

GB           24140 A     6/1913
JP         S632620 B2    1/1988
(Continued)

OTHER PUBLICATIONS

International Search Report and Written Opinion for International Application No. PCT/JP2019/015929, dated Jun. 25, 2019, 7 pages.
(Continued)

*Primary Examiner* — Robert H Muromoto, Jr.
(74) *Attorney, Agent, or Firm* — RatnerPrestia (57) ABSTRACT

Provided is a tubular fabric that has a homogeneous structure along its outer circumference and excellent shape-stability and that is useful as hoses for transferring a fluid or powder or for protecting linear materials such as a wire, a cable, and a conduit, tubular filters, and medical base materials such as an artificial blood vessel. The tubular fabric includes a wall part that is woven by interlacing a warp yarn and a weft yarn and that has a double weave structure, a weft yarn in an outer layer and a weft yarn in an inner layer being not intersected with each other. The tubular fabric preferably has a circularity c of 0.8 or more and 1.2 or less, the circularity c being represented by the following
(Continued)

equation of an outer diameter b perpendicular to an outer diameter a with respect to the outer diameter a, the outer diameter a being obtained by measuring a location corresponding to a fabric width A in weaving of the tubular fabric.

Circularity $c=a/b$.

11 Claims, 6 Drawing Sheets

(51) Int. Cl.
  *D03D 1/00* (2006.01)
  *A61F 2/06* (2013.01)

(56) References Cited

U.S. PATENT DOCUMENTS

| | | | | |
|---|---|---|---|---|
| 4,602,911 | A * | 7/1986 | Ahmadi | A61F 2/2445 |
| | | | | 623/2.37 |
| 5,273,080 | A | 12/1993 | Morohashi et al. | |
| 5,496,364 | A * | 3/1996 | Schmitt | D03D 3/02 |
| | | | | 623/1.52 |
| 5,697,969 | A * | 12/1997 | Schmitt | A61F 2/06 |
| | | | | 600/36 |
| 5,883,022 | A * | 3/1999 | Elsener | A47K 10/02 |
| | | | | 442/192 |
| 9,943,424 | B2 * | 4/2018 | Yamada | A61L 33/068 |
| 10,070,949 | B2 * | 9/2018 | Tsuchikura | A61F 2/0077 |
| 10,751,507 | B2 * | 8/2020 | Palmer | A61M 25/0045 |
| 2002/0151823 | A1 * | 10/2002 | Miyata | A61M 25/09 |
| | | | | 600/585 |
| 2006/0009835 | A1 * | 1/2006 | Osborne | A61F 2/07 |
| | | | | 623/1.13 |
| 2006/0009839 | A1 * | 1/2006 | Tan | A61F 2/06 |
| | | | | 623/1.38 |
| 2012/0171917 | A1 * | 7/2012 | Rasmussen | D03D 15/00 |
| | | | | 442/199 |
| 2013/0035014 | A1 * | 2/2013 | Tone | D03D 13/008 |
| | | | | 442/189 |
| 2013/0041452 | A1 * | 2/2013 | Fujita | D04B 21/16 |
| | | | | 623/1.13 |
| 2015/0203995 | A1 * | 7/2015 | Adams | D03D 15/513 |
| | | | | 2/455 |
| 2016/0058588 | A1 * | 3/2016 | Yamada | A61L 33/068 |
| | | | | 623/1.16 |
| 2016/0135944 | A1 * | 5/2016 | Saito | A61L 27/507 |
| | | | | 623/1.13 |
| 2017/0182752 | A1 * | 6/2017 | Callhoff | B32B 27/40 |
| 2017/0183873 | A1 * | 6/2017 | Vido | B32B 27/36 |
| 2017/0252617 | A1 * | 9/2017 | Caron Kardos | B32B 5/08 |
| 2018/0289925 | A1 * | 10/2018 | Palmer | A61M 25/005 |

FOREIGN PATENT DOCUMENTS

| | | |
|---|---|---|
| JP | 63196889 U | 12/1988 |
| JP | 055242 A | 1/1993 |
| JP | 06184857 A | 7/1994 |
| JP | 0880342 A | 3/1996 |
| JP | 2779456 B2 | 7/1998 |
| JP | 2005261867 A | 9/2005 |
| JP | 2009270236 A | 11/2009 |
| WO | 2018066476 A1 | 4/2018 |

OTHER PUBLICATIONS

Hirotsu et al., "Development of Special Seamless Textiles", Journal of the Textile Machinery Society, 2007, vol. 60, No. 10, with translation, pp. 567-570.

Extended European Search Report for European Application No. 19 793 795.6. dated Dec. 17, 2021, 7 paqes.

* cited by examiner

TUBULAR FABRIC AND BASE MATERIAL FOR MEDICAL USE USING SAME

CROSS REFERENCE TO RELATED APPLICATIONS

This is the U.S. National Phase application of PCT/JP2019/015929, filed Apr. 12, 2019, which claims priority to Japanese Patent Application No. 2018-085164, filed Apr. 26, 2018, the disclosures of each of these applications being incorporated herein by reference in their entireties for all purposes.

FIELD OF THE INVENTION

The present invention relates to a tubular fabric. The present invention more specifically relates to a tubular fabric that includes a wall part having a double weave structure.

BACKGROUND OF THE INVENTION

Tubular fabrics are being used for various industrial applications such as a hose, a reinforcing material, and a protection material, and multilayer-structure fabrics are being proposed having a complicated weave structure according to the application.

For example, Patent Document 1 proposes a thick belt that is formed of four or more layers and is a bag-shaped fabric formed using two weft shuttles.

Patent Document 2 proposes a two-pronged tube-shaped fabric produced using a needle loom, and Patent Document 3 proposes an artificial blood vessel tubularly woven using one weft yarn.

Further, Patent Document 4 discloses a two-layer tubular fabric that is less uneven on an inner surface of the tubular fabric, has excellent stretchability, softness, and kink resistance (easy flexibility), and is suitable for artificial blood vessels.

PATENT DOCUMENTS

Patent Document 1: Japanese Patent Laid-open Publication No. 06-184857
Patent Document 2: Japanese Patent Laid-open Publication No. 08-80342
Patent Document 3: Japanese Patent No. 2779456
Patent Document 4: WO 2018/066476 A

SUMMARY OF THE INVENTION

However, the multilayer-structure fabric of Patent Document 1 is woven in a bag shape but is not one utilized after processing into a tubular shape. Further, the shuttles of the loom are placed back and forth, forcing the weft yarn fed by the back shuttle to always pass only above or below the front shuttle to give a fabric always having intersection of the weft yarns at either one of the left or the right of the fabric. Therefore, weaving in a tubular shape leads to a result of impairing, at the intersection portion, the homogeneity along the outer circumference of the tubular fabric. For example, a tubular fabric, such as an artificial blood vessel, produced using this technique has had a possibility of varying the property of puncture along the outer circumference.

On the other hand, the tube-shaped fabric described in Patent Document 2 is a technique for weaving a two-pronged tube-shaped fabric by alternately inserting a first needle and a second needle of a needle loom. The tube-shaped fabric, however, includes one layer as a fabric layer, so that the technique also has a problem of shape-stability.

The self-supporting tube-shaped knitted or woven artificial blood vessel described in Patent Document 3 has a plain-weave structure and is formed of one layer as a structure, so that the technique also has a problem of shape-stability.

Further, weaving of the tubular fabric described in Patent Document 4 with a normal shuttle loom causes mutual intersection of weft yarns in layers, so that the intersection portion has similarly had poor homogeneity along the outer circumference.

Accordingly, an object of the present invention is to provide a tubular fabric that has a homogeneous structure along its outer circumference and that includes an excellent shape-stability wall part having a double weave structure.

In order to solve the above problems, the present invention according to exemplary embodiments is configured as follows.

(1) A tubular fabric including a wall part that is woven by interlacing a warp yarn and a weft yarn and has a double weave structure, in which a weft yarn in an outer layer and a weft yarn in an inner layer are not intersected with each other.

(2) The tubular fabric according to (1), having a circularity c of 0.8 or more and 1.2 or less, in which the circularity c is represented by a following equation 1 of an outer diameter b perpendicular to an outer diameter a with respect to the outer diameter a, and the outer diameter a is obtained by measuring a location corresponding to a fabric width A in weaving of the tubular fabric.

$$\text{Circularity } c=a/b \qquad \text{(equation 1)}$$

(3) The tubular fabric according to (1) or (2), having a repulsive ratio Fc of 0.8 or more and 1.2 or less, in which the repulsive ratio Fc is represented by a following equation 2 of a repulsive force Fb under compression along the outer diameter b of the tubular fabric by a distance one-half the outer diameter b with respect to a repulsive force Fa under compression along the outer diameter a of the tubular fabric by a distance one-half the outer diameter b.

$$\text{Repulsive ratio } Fc=Fa/Fb \qquad \text{(equation 2)}$$

(4) The tubular fabric according to any one of (1) to (3), satisfying a following equation 3.

$$(L2-L1)/L1 \geq 0.1 \qquad \text{(equation 3)}$$

L1 is a gauge-line distance between gauge lines that is obtained under compression in a warp direction of the tubular fabric at a stress of 0.01 cN/dtex, the gauge lines being drawn on an outer circumference of the tubular fabric, with a distance five times a maximum value of an outer diameter of the tubular fabric measured without application of a stress to the tubular fabric.

L2 is a gauge-line distance under elongation in the warp direction at a stress of 0.01 cN/dtex.

(5) The tubular fabric according to any one of (1) to (4), having no accordion structure.

(6) The tubular fabric according to any one of (1) to (5), in which the warp yarn and the weft yarn used in the tubular fabric are synthetic fibers.

(7) The tubular fabric according to any one of (1) to (6), in which the synthetic fibers used as the warp yarn and/or the weft yarn are polyester having a fracture elongation of 70% or less.

(8) The tubular fabric according to any one of (1) to (7), in which a synthetic fiber exposed to an inner surface constituting the tubular fabric is a multifilament whose single-yarn diameters are partially or entirely 5 µm or less.

(9) The tubular fabric according to any one of (1) to (8), in which synthetic fibers in the outer layer constituting the tubular fabric are partially or entirely monofilaments having a diameter of 20 µm or more.

(10) A medical base material containing the tubular fabric according to any one of (1) to (9).

According to the present invention, a tubular fabric is obtained that has a homogeneous structure along its outer circumference and that includes an excellent shape-stability wall part having a double weave structure. According to a further preferable aspect of the present invention, a tubular fabric is obtained that has an almost true circle as the sectional shape and that further has a good shape-retaining ability.

The tubular fabric of the present invention is usefully applicable to hoses for transferring a fluid or powder or for protecting linear materials such as a wire, a cable, and a conduit, tubular filters, and medical base materials such as an artificial blood vessel, a shunt, and a stent graft. A medical base material of the present invention has a homogeneous structure along the outer circumference of the tubular fabric when grafted as an artificial blood vessel, has the same property of puncture in any location to allow easy sewing, and also has an excellent shape-retaining ability to enable rapid suture in an operation. According to a further preferable aspect of the present invention, the tubular fabric has an almost true circle as its sectional shape to have more excellent ease of sewing and a more excellent shape-retaining ability and thus exhibit a more excellent effect in an operation.

DETAILED DESCRIPTION OF EMBODIMENTS OF THE INVENTION

A tubular fabric according to embodiments of the present invention is a tubular fabric including a wall part that is woven by interlacing a warp yarn and a weft yarn and that has a double weave structure, the tubular fabric being characterized in that a weft yarn in an outer layer and a weft yarn in an inner layer are not intersected with each other.

The phrase "the weft yarns in the layers are not intersected with each other" means that the weft yarn placed in the outer layer and the weft yarn placed in the inner layer are not interlaced when a double weft fabric is tubularly woven, to allow no inner-layer weft yarn to appear on a surface of the tubular fabric. The term "double weave structure" means that the weave structure is double and refers to double weft weave where the weft yarn is double and to double warp and weft weave where both the warp yarn and the weft yarn are double.

The tubular fabric configured above has a homogeneous structure along the outer circumference of a section across the long axis at the tubular wall part having the double weave structure, and has excellent shape-stability. Particularly, when grafted as an artificial blood vessel, the tubular fabric has the same property of puncture in any location along the outer circumference of the tubular fabric and has excellent shape-stability to allow easy sewing.

It is preferable to use a synthetic fiber for the warp yarn and the weft yarn used in the tubular fabric of the present invention. Specific examples of such a synthetic fiber include a nylon fiber and a polyester fiber, and a polyester fiber is preferable in terms of strength and dimensional stability. Examples of the polyester fiber include a fiber formed of, for example, polyethylene terephthalate, polybutylene terephthalate, polypropylene terephthalate, or a copolymer thereof.

The synthetic fiber preferably has a fracture elongation of 70% or less in terms of strength and shape-stability. The synthetic fiber has a fracture elongation of further preferably 60% or less, more preferably 50% or less, and the lower limit is 10% or more.

The fiber constituting the warp yarn in the tubular fabric has a total fineness of preferably 560 dtex or less, further preferably 235 dtex or less, more preferably 100 dtex or less, in terms of strength and shape-stability, and the lower limit is 10 dtex or more.

The weave density based on a warp yarn A that is measured by cutting open the tubular fabric is preferably 200 yarns/inch (2.54 cm) or less, further preferably 180 yarns/inch (2.54 cm) or less, more preferably 150 yarns/inch (2.54 cm) or less, in terms of strength and shape-stability, and the lower limit is 20 yarns/inch (2.54 cm) or more.

The fiber constituting the weft yarn in the tubular fabric has a total fineness of preferably 560 dtex or less, further preferably 235 dtex or less, more preferably 100 dtex or less, in terms of strength and shape-stability, and the lower limit is 10 dtex or more.

The weave density based on each of the inner-layer weft yarn and the outer-layer weft yarn that is measured by cutting open the tubular fabric is preferably 200 yarns/inch (2.54 cm) or less, further preferably 180 yarns/inch (2.54 cm) or less, more preferably 150 yarns/inch (2.54 cm) or less, in terms of strength and shape-stability, and the lower limit is 20 yarns/inch (2.54 cm) or more.

The tubular fabric has an inner diameter of preferably 100 mm or less, further preferably 50 mm or less, more preferably 10 mm or less, in terms of shape-stability. A preferable lower limit is about 1.5 mm in terms of weaving performance.

The method for producing the tubular fabric of the present invention is not particularly limited as long as the method gives the tubular fabric specified in the present invention. The tubular fabric of the present invention, however, is preferably woven using a shuttle loom with two or more shuttles placed back and forth on the cloth-fell end and the beam end of the loom, so as to form a tubular wall part having the double weave structure. That is, the tubular fabric is preferably woven so as to form a quadruple fabric having a quadruple weave structure, with no connection point provided but a hollow formed between the second layer and the third layer. In the weaving, a total of two shuttles are used that are a shuttle for weft insertion of the weft yarn constituting the outer layer (hereinafter also sometimes referred to as an outer-layer weft yarn) and a shuttle for weft insertion of the weft yarn constituting the inner layer (hereinafter also sometimes referred to as an inner-layer weft yarn). Each of the shuttles are used for weft insertion while allowed to make a round trip on a rail.

In the weaving of the tubular fabric, when the weft insertion is performed by conventional methods with respect to a shedding part between the warp yarns, using the shuttles placed back and forth on the cloth-fell end and the beam end, with the cloth-fell-end shuttle used for the inner layer and the beam-end shuttle used for the outer layer of the tubular fabric, the weft yarn supplied by the back shuttle always passes above the cloth-fell-end shuttle to cause the inner-layer weft yarn to be intersected with the outer-layer weft yarn and thus be exposed on a surface of the tubular fabric. However, switching the positions of the front and back shuttles in the weft insertion causing the exposure of the inner-layer weft yarn enables weft insertion causing no intersection of the inner-layer weft yarn with the outer-layer weft yarn.

Figure 1:
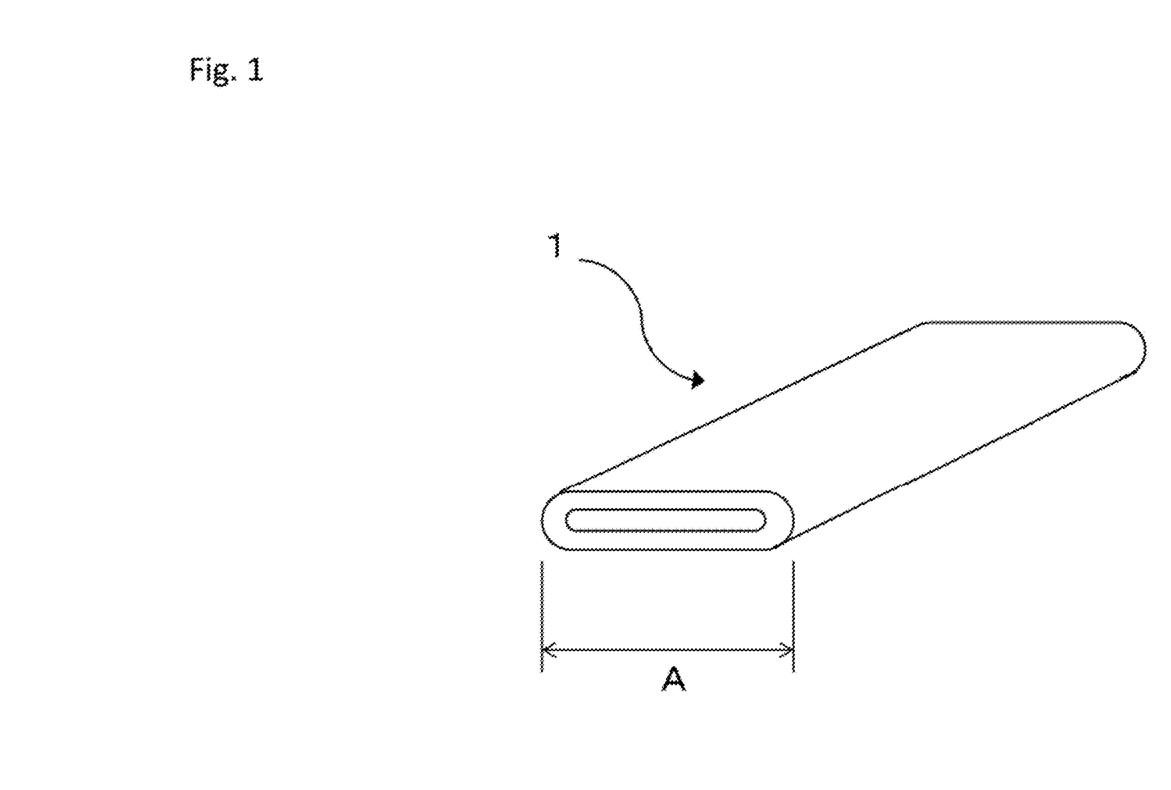
FIG. 1 is an explanatory diagram of a gray fabric completely woven as a tubular fabric.
Figure 2:
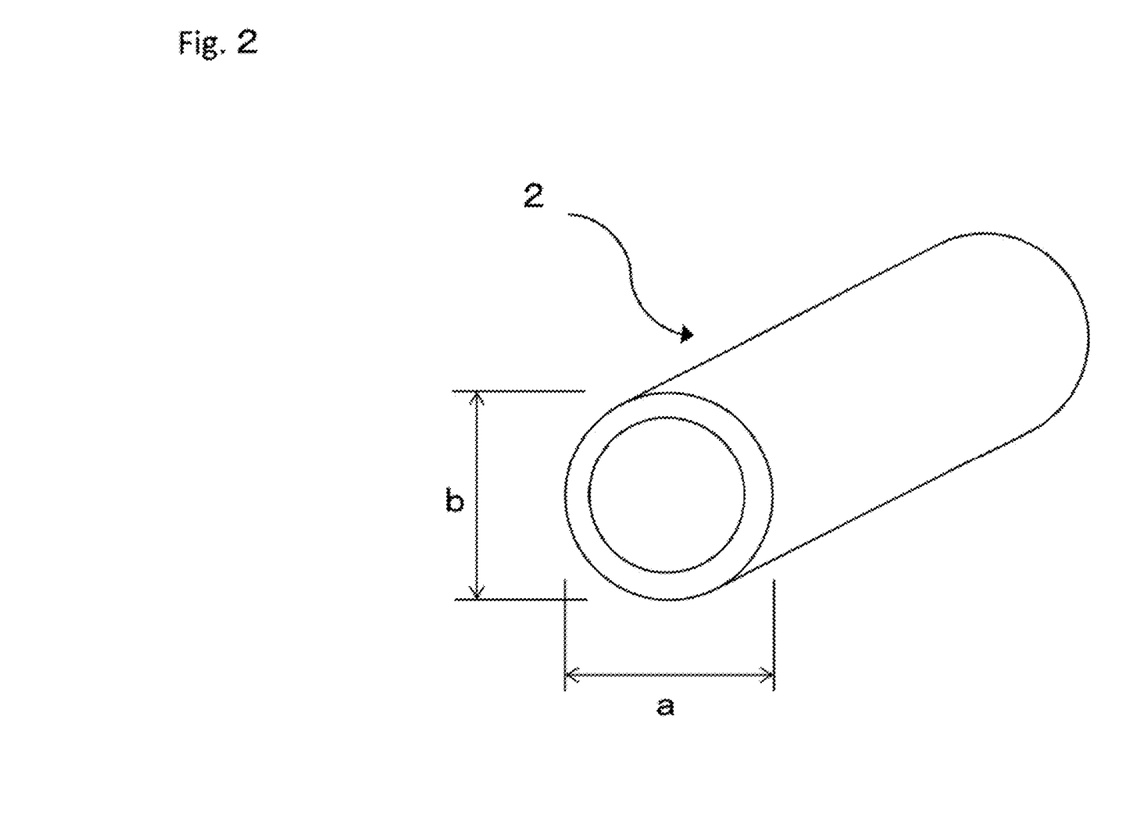
FIG. 2 is an explanatory diagram of a base material obtained by completely processing the tubular fabric.

Further, the tubular fabric of the present invention preferably has a circularity c of 0.8 or more and 1.2 or less, more preferably 0.85 or more and 1.15 or less, the circularity c being represented by the following equation of an outer diameter b perpendicular to an outer diameter a with respect to the outer diameter a, the outer diameter a being obtained by measuring, in a tubular fabric 2 processed as shown in FIG. 2, a location corresponding to a fabric width A in the weaving of a tubular fabric (gray fabric) 1 as shown in FIG. 1.

Circularity $c = a/b$

Setting the relationship between the outer diameters a and b in the above range leads to the tubular fabric being a true circle or having a shape close to the true circle, to enable provision of the tubular fabric allowing easy sewing with a tubular material having the same diameter.

In embodiments of the present invention, the cross-sectional outer circumferential part of the wall part constituting the tubular fabric has a homogeneous structure, so that appropriate adjustment of the material and the fineness of the fiber, the weave density, and the outer diameter and the inner diameter of the tubular fabric so as to impart proper repulsive force to the tubular fabric enables an improvement in the circularity of the cross-sectional outer circumferential part. The repulsive force can be increased, for example, by using a stiffer fiber as the material for the fiber or by increasing the single-yarn fineness, the total fineness, or the weave density. It is possible to increase the repulsive force by forming the tubular fabric with use of, for example, a fiber having a high single-yarn fineness, e.g., a monofilament (a diameter of preferably 20 μm or more, more preferably 40 μm or more, and the upper limit is 150 μm or less). Further, by forming the tubular fabric with use of fibers at least a part of which is a fiber having a low single-yarn fineness, it is possible to make the structure homogeneous and dense, thus improving the homogeneity of the cross-sectional outer circumferential part of the wall part and thus also increase the circularity. The fiber having a low single-yarn fineness described above is preferably a multifilament whose single-yarn diameters are partially or entirely 5 μm or less. The single-yarn diameter is more preferably 4 μm or less, and the lower limit is 1 μm or more. Setting the single-yarn diameter in the above range improves the softness of the tubular fabric to enable formation of a denser structure. Further, it is also possible to further increase the repulsive force and thus increase the circularity by a method for using a fiber having a high single-yarn fineness, e.g., a monofilament (preferably a diameter of 20 μm or more, more preferably 40 μm or more, and the upper limit is 150 μm or less) in combination with the above or by a method for decreasing the outer diameter or the inner diameter of the tubular fabric. Then, a round rod having an outer diameter fitted to the dimension of the inner diameter of these woven tubular fabrics is inserted into a hollow of the tubular fabric and the tubular fabric is heat-set to be shrunk and thus be set in a shape along the round rod, so that the tubular fabric having a circularity in the above range can easily be obtained.

A heat-setting condition is preferably 60° C. or more higher, more preferably 80° C. or more higher than the glass transition temperature of the material used, and is preferably 20° C. or more lower, more preferably 30° C. or more lower than the melting point of the material used. Setting the heat-setting temperature in the above range allows an excellent heat setting property and proper shrinkage to enable formation of the shape along the shape of the core rod and thus acquisition of the tubular fabric having excellent shape-stability.

Further, the ratio of a repulsive force Fb under compression along the outer diameter b of the tubular fabric by a distance one-half the outer diameter b to a repulsive force Fa under compression along the outer diameter a of the tubular fabric by a distance one-half the outer diameter a, that is, the repulsive ratio Fc represented by the following equation is preferably 0.8 or more and 1.2 or less, more preferably 0.85 or more and 1.15 or less.

Repulsive ratio $Fc = Fa/Fb$

Setting the relationship between the repulsive forces Fa and Fb in the above range enables provision of the tubular fabric having an excellent shape-retaining ability and has excellent kink resistance (easy flexibility) even when flexed.

In embodiments of the present invention, the cross-sectional outer circumferential part of the wall part constituting the tubular fabric has a homogeneous structure to enable acquisition of the tubular fabric having small anisotropic repulsive force. Appropriate adjustment of the weave density, and the outer diameter and the inner diameter of the tubular fabric so as to give further proper repulsive force enables a much more decrease of the repulsive ratio. Then, a round rod having an outer diameter fitted to the dimension of the inner diameter of the tubular fabric woven is inserted into a hollow of the tubular fabric and the tubular fabric is heat-set to be shrunk and thus increase the repulsive force, so that the tubular fabric having a repulsive ratio in the above range can easily be obtained.

Further, the tubular fabric according to embodiments of the present invention is characterized in that the relationship between a gauge-line distance L1 between gauge lines and a gauge-line distance L2 between the gauge lines is represented by the following equation, the gauge lines being drawn with a distance five times the outer-diameter maximum part of the tubular fabric measured without application of a stress to the tubular fabric, the gauge-line distance L1 being a gauge-line distance under compression in a warp direction of the tubular fabric at a stress of 0.01 cN/dtex, and the gauge-line distance L2 being a gauge-line distance under elongation in the warp direction at a stress of 0.01 cN/dtex.

$(L2-L1)/L1 \geq 0.1$

The value of the formula $(L2-L1)/L1$ is preferably 0.15 or more, more preferably 0.18 or more, in terms of further improving the stretchability and the softness of the tubular fabric. The upper limit is preferably 1.0.

Setting the relationship between the gauge-line distances L1 and L2 in the above range enables provision of the tubular fabric having excellent stretchability, softness, and kink resistance (easy flexibility). That is, when the tubular fabric is bent to be flexed, a stress is applied onto an inner circumferential side of the flexed tubular fabric in the compression direction and simultaneously onto an outer circumferential side in the elongation direction. Setting the relationship in the above range, however, enables the outer circumference to be sufficiently elongated with respect to the inner circumference, which means that the tubular fabric has excellent kink resistance. An elongation operation or a compression operation at a stress of 0.01 cN/dtex corresponds to a stress normally generated when a person manually elongates or compresses the tubular fabric with a soft touch in the warp direction, and the tubular fabric having a relationship in the above range means that the tubular fabric has good operability also in a flexure operation performed by a person and has excellent stretchability and softness. In the tubular fabric designed so as to have stretchability and softness as described above, designing the weft yarns in the layers not to be intersected with each other makes the tubular fabric more effective than a tubular fabric having a similar weave design, in terms of further improving the stretchability represented by (L2−L1)/L1.

The tubular fabric of the present invention preferably has an elongation of 30% or less when elongated at a stress of 0.01 cN/dtex in the warp direction, in terms of allowing a person to feel a response when manually pulling the tubular fabric with a soft touch. The tubular fabric has an elongation of further preferably 20% or less, more preferably about 10%. The tubular fabric has, as the lower limit, an elongation of preferably 5% or more, more preferably 8% or more, in terms of allowing a person to feel a sense of elongation when manually pulling the tubular fabric with a soft touch. The tubular fabric having an elongation in the above range has good operability for allowing a person to manually perform sewing and is soft, so that the tubular fabric has the same property of puncture in any location along the outer circumference of the tubular fabric when grafted as an artificial blood vessel.

The tubular fabric preferably has no accordion structure. The tubular fabric having no accordion structure has no unevenness on the inner surface, generating no turbulent flow even when a fluid is flowed in a narrow space and generating no turbulent flow of blood when used as a particularly narrow artificial blood vessel or shunt, to have an advantage of being less likely to produce a blood clot.

The phrase "having no accordion structure" refers to a tubular fabric having no structure obtained by inserting a core rod with a spiral or annular wave groove into the tubular fabric and heating the tubular fabric for wave setting or to a non-pleated tubular fabric. For formation of the tubular fabric having no accordion structure, it is desirable to finish the tubular fabric without using the core rod with a spiral or annular wave groove described above. Particularly, the tubular fabric is preferably heat-set using a round rod as the core rod inserted.

Further, in embodiments of the present invention, use of a fiber having a low elongation, for example, a fracture elongation of 70% or less as a fiber used in the tubular fabric also enables impartation of the stretchability to the tubular fabric itself.

Such a tubular fabric can be produced as follows, for example.

In a weaving step, as the warp yarns, at least two types of yarns (a warp yarn A and a warp yarn B) are preferably used. These warp yarns are also preferably fibers having a fracture elongation of 70% or less as described above. The fibers have a fracture elongation of further preferably 60% or less, more preferably 50% or less, and the lower limit is 10% or more. Such fibers are different from an elastic yarn having so-called rubber elasticity and are normally recognized as non-elastic yarns in this industry.

The warp yarn A can be formed of various synthetic fibers such as a nylon fiber and a polyester fiber. Especially, a polyester fiber that is a non-elastic yarn is preferable in terms of strength and dimensional stability. Examples of the polyester fiber that is a non-elastic yarn include a fiber formed of, for example, polyethylene terephthalate, polybutylene terephthalate, polypropylene terephthalate, or a copolymer thereof.

Here, the warp yarn A that is a synthetic fiber exposed to the inner surface constituting the tubular fabric may be an ultrathin fiber obtained by direct spinning or may be an ultrathin fiber obtained by subjecting a sea-island composite fiber to a sea removal treatment. Especially, the synthetic fiber in the warp direction that is exposed to the inner surface is preferably a multifilament whose single-yarn diameters are partially or entirely 5 μm or less. Setting the single-yarn diameters in the above range improves the softness of the tubular fabric and enables formation of a denser structure, so that the tubular fabric can be expected to cover an endothelial cell when used as an artificial blood vessel or a shunt.

The warp yarn B is preferably formed of a soluble yarn. The soluble yarn is a fiber soluble in solvents such as water and an alkaline solution. As specific examples of the soluble yarn, it is possible to use water-soluble fibers such as a polyvinyl alcohol fiber; and easily alkali-soluble fibers such as a polyester fiber containing a third copolymerized component, i.e., isophthalic acid, 5-sodiumsulfoisophthalic acid, or methoxy polyoxyethylene glycol, and a polylactic acid fiber. The soluble yarn, however, is not particularly limited. As the warp yarn B, it is also possible to use a temporary yarn to be removed after weaving.

The warp yarns each have a total fineness of preferably 560 dtex or less, further preferably 235 dtex or less, more preferably 100 dtex or less, and the lower limit is 10 dtex or more.

The weave density based on the warp yarn A that is measured by cutting open the tubular fabric of the present invention is preferably 200 yarns/inch (2.54 cm) or less, further preferably 180 yarns/inch (2.54 cm) or less, more preferably 150 yarns/inch (2.54 cm) or less, and the lower limit is 20 yarns/inch (2.54 cm) or more.

As the weft yarns, at least two types of yarns (a weft yarn C and a weft yarn D) are preferably used.

In this case, a tubular fabric having a double structure is preferably formed. A preferable aspect of this case is that the weft yarn C is positioned in the inner layer, and the weft yarn D is position in the outer layer of the tubular fabric.

The weft yarn C positioned in the inner layer and the weft yarn D positioned in the outer layer are, for example, formed of various synthetic fibers such as a nylon fiber and a polyester fiber but are preferably non-elastic yarns. Especially, a polyester fiber that is a non-elastic yarn is preferable in terms of strength and dimensional stability. Examples of the polyester fiber that is a non-elastic yarn include a fiber formed of, for example, polyethylene terephthalate, polybutylene terephthalate, or polypropylene terephthalate.

The yarns have a fracture elongation of preferably 70% or less, further preferably 60% or less, more preferably 50% or less, and the lower limit is 10% or more.

The weft yarn C positioned in the inner layer and exposed to the inner surface can be an ultrathin fiber obtained by subjecting a sea-island composite fiber to a sea removal treatment or by direct spinning, using, as an original yarn, the sea-island composite fiber or the ultrathin fiber obtained by direct spinning. These synthetic fibers as the weft yarn C are each preferably a multifilament whose single-yarn diameters are partially or entirely 5 μm or less. The single-yarn diameter is more preferably 4 μm or less, and the lower limit is 1 μm or more. Setting the single-yarn diameter in the above range improves the softness of the tubular fabric and enables formation of a denser structure, so that the tubular fabric can be expected to be covered by an endothelial cell when used as an artificial blood vessel or a shunt.

The weft yarn D positioned in the outer layer is preferably a monofilament having a single-yarn diameter of 20 μm or more. The weft yarn D has a single-yarn diameter of more preferably 40 μm or more, and the upper limit is 150 μm or less. Setting the single-yarn diameter in the above range improves the stiffness of the inner layer and thus improves the repulsive force of the tubular fabric. Setting the single-yarn diameter in the above range also suppress degradation of the tubular fabric caused by hydrolysis to enable an improvement of the durability of the tubular fabric.

The weft yarns each have a total fineness of preferably 560 dtex or less, further preferably 235 dtex or less, more preferably 100 dtex or less, and the lower limit is 10 dtex or more.

The weave density based on each of the weft yarns C and D that is measured by cutting open the post-processed tubular fabric is preferably 200 yarns/inch (2.54 cm) or less, further preferably 180 yarns/inch (2.54 cm) or less, more preferably 150 yarns/inch (2.54 cm) or less, and the lower limit is 20 yarns/inch (2.54 cm) or more.

The weft insertion method for not causing intersection between the inner-layer weft yarn and the outer-layer weft yarn in the weaving of the tubular fabric is, for example, a method for using a shuttle loom with two or more shuttles placed back and forth on the cloth-fell end and the beam end of the loom and switching the positions of the front and back shuttles in the weft insertion causing the exposure of the inner-layer weft yarn.

In the weaving, the tubular fabric is preferably woven, with the warp yarn B placed at high tension, and the warp yarn A placed at low tension within a range not to adversely affect the shed of the loom. For example, the warp yarn B preferably has a tension of 0.5 to 1.5 cN/dtex, and the warp yarn A preferably has a tension of 0.05 to 0.15 cN/dtex. The placement of the warp yarns A and B is preferably placement at a ratio of the warp yarn A to the warp yarn B of 2 to 10 yarns/1 yarn.

As regards a high-density fabric, lowering the tension of the warp yarn in the weaving to increase the crimp ratio of the warp yarn generally makes it difficult to increase the weft density due to bumping (slack pick). The embodiment described above, however, enables the weft yarn to be firmly held by the warp yarn A while the warp yarn B serving as a fulcrum, and thus enables suppression of the bumping. Therefore, the crimp ratio of the warp yarn A can be increased, and removal of the warp yarn B after the weaving enables impartation of the softness to the tubular fabric.

The warp yarn B is preferably placed between the weft yarn C positioned in the inner layer and the weft yarn D positioned in the outer layer.

The use of at least two types of weft yarns, i.e., the weft yarn C position in the inner layer and the weft yarn D positioned in the outer layer of the tubular fabric generates structural strain due to their different perimeters. The structural strain enables impartation of an elongation property to the tubular fabric. According to the embodiment described above, the weft yarns C and D are not intersected with each other to enable the cross-sectional outer circumferential part of the wall part to have a homogeneous structure, so that the tubular fabric has the same property of puncture in any location along the outer circumference of the tubular fabric when grafted as an artificial blood vessel, and has excellent shape-stability.

The tubular fabric has an inner diameter of preferably 100 mm or less, further preferably 50 mm or less, more preferably 10 mm or less. A preferable lower limit is about 1.5 mm in terms of weaving performance.

The post-processing step preferably includes the following steps, for example. In the following embodiment, an example is a tubular fabric having an inner diameter of 3.3 mm.

(a) Hot Water Washing

Hot water washing removes original-yarn oil and shrink the warp yarn B. The treatment conditions are preferably a temperature of 80 to 98° C. and a time of 15 to 40 minutes.

(b) Pre-Heat Setting

Pre-heat setting stabilizes the shape of the warp yarn A having increased its crimp ratio along with the shrinkage of the warp yarn B. A round rod having an outer diameter of 3.0 mm is inserted into the tubular fabric, and the tubular fabric is fixed at both ends with a wire or the like, and heat-treated. The outer diameter of the round rod used is appropriately selected according to the degree of shrinkage of the woven tubular fabric by the pre-heat setting. The treatment conditions are preferably a temperature of 160 to 190° C. and a time of 3 to 10 minutes. The material for the round rod is, for example, steel use stainless (SUS).

(c) Sea Removal Treatment

The warp yarn A and the weft yarn C are subjected to a sea removal treatment as necessary, and the warp yarn B is removed by dissolution.

The sea removal treatment and the removal by dissolution are performed by the following steps.

(c-1) Acid Treatment

An acid treatment embrittles a sea component of the sea-island composite fiber. The acid is, for example, maleic acid. The treatment conditions are preferably a concentration of 0.1 to 1% by mass, a temperature of 100 to 150° C., and a time of 10 to 50 minutes. When the sea-island composite fiber is not used, the acid treatment can be avoided.

(c-2) Alkali Treatment

An alkali treatment elutes the soluble yarn and the sea component of the sea-island composite fiber having been embrittled. The alkali is, for example, sodium hydroxide. The treatment conditions are preferably a concentration of 0.5 to 2% by mass, a temperature of 70 to 98° C., and a time of 60 to 100 minutes.

(d) Heat Setting 1 (First Time)

First heat setting is aimed at re-maximizing the crimps of the warp yarn loosened by the sea removal treatment. A round rod having an outer diameter of 3.3 mm is inserted into the tubular fabric, and the tubular fabric is fixed at both ends with a wire or the like while maximally compressed in the warp direction so as not to allow wrinkles on the tubular fabric, and is heat-treated. The treatment conditions are preferably a temperature of 160 to 190° C. and a time of 3 to 10 minutes. The material for the round rod is, for example, steel use stainless (SUS).

(e) Heat Setting (Second Time)

Second heat setting is aimed at forming a fabric that has a shrinkage margin while retaining flexing points of the crimps. The second heat setting, however, need not be performed. A round rod having an outer diameter of 3.3 mm is inserted into the tubular fabric, and the tubular fabric is fixed at both ends with a wire or the like while elongated by 20 to 50% in the warp direction, and is heat-treated. The treatment conditions are preferably a temperature of 10 to 20° C. lower than in the first heat setting, and a time of 3 to 10 minutes. The round rod is, for example, SUS.

The tubular fabric obtained as described above includes the wall part whose cross-sectional outer circumferential part has a homogeneous structure, and the tubular fabric has excellent shape-stability. In a particularly preferable aspect, the tubular fabric has an almost true circle as the shape of a section cut along the diameter, is less uneven on the inner surface, and has excellent stretchability, softness, kink resistance (easy flexibility), shape-retaining ability, and repulsive force, and the tubular fabric is usefully applicable to hoses for transferring a fluid or powder or for protecting linear materials such as a wire, a cable, and a conduit, tubular filters, and medical base materials such as an artificial blood vessel and is suitably usable particularly as an artificial blood vessel.

EXAMPLES

Hereinafter, the present invention is described with reference to examples and comparative examples.

The methods for measuring various properties used in the present examples are as follows.

(1) Fineness and Number of Filaments

The fineness was measured in compliance with fineness based on corrected mass (method A) in JIS L 1013: 2010 8.3.1.

The number of filaments was measured on the basis of JIS L 1013: 2010 8.4.

(2) Single-Yarn Diameter

The single-yarn diameter was measured on the basis of a photograph of lateral surfaces of single yarns in a multifilament used and a lateral surface of a monofilament used, the photograph being taken with microscope VHX-200 (manufactured by KEYENCE CORPORATION) at 100 to 400-fold magnification. The single-yarn diameter was calculated in the unit of μm. In the measurement, a modified cross-section yarn such as a flat yarn was measured at the part where its lateral surface was minimum.

(3) Inner Diameter of Tubular Fabric

The inner diameter of the tubular fabric was measured in accordance with the guidance of ISO7198 by vertically standing a circular cone with a taper ratio of 1/10 or less, vertically and softly dropping the tubular fabric onto the circular cone so that the section cut along the diameter of the tubular fabric covered the circular cone, and measuring the diameter of the circular cone at the position where the lower end of the sample stopped.

The tubular fabric was cut at 50-mm intervals in the warp direction, measured at five locations, and evaluated according to the average of the measured values.

(4) Outer Diameter of Tubular Fabric

The outer diameter of the tubular fabric was measured with a caliper.

The tubular fabric was measured at five locations with 50-mm intervals in the warp direction without application of a stress to the tubular fabric, and evaluated according to the average of the measured values.

(5) Repulsive Force of Tubular Fabric

Figure 3:
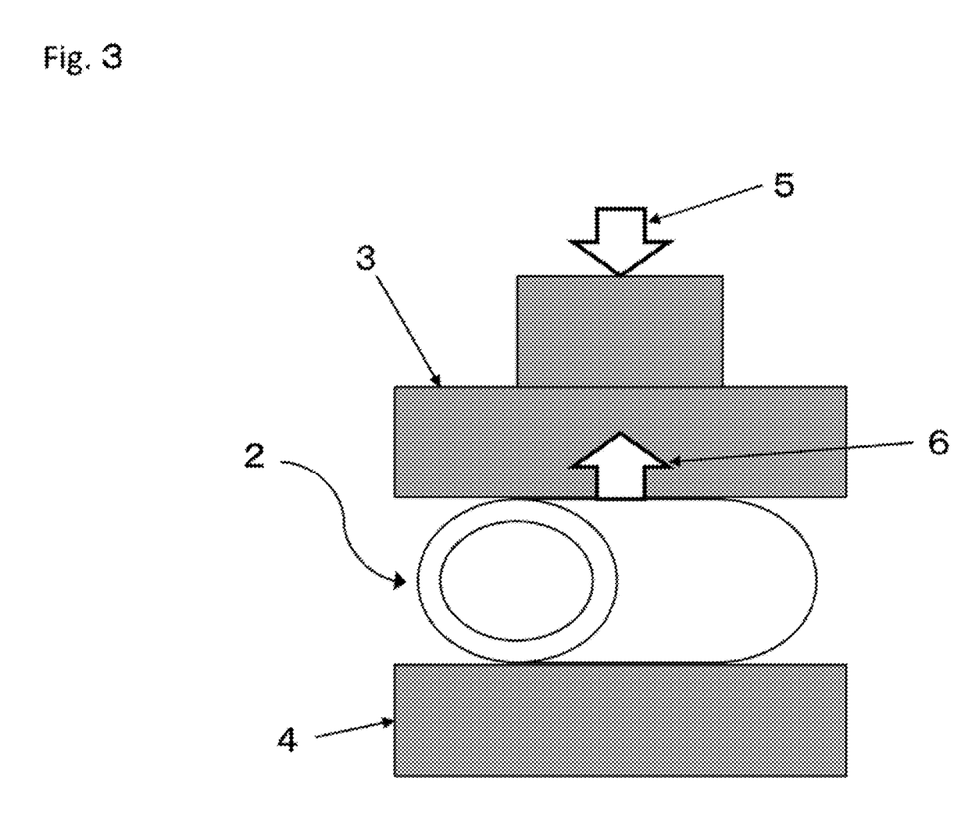
FIG. 3 is a conceptual diagram of a device for measuring the repulsive force of the tubular fabric.

FIG. 3 is a conceptual diagram of a device for measuring the repulsive force of the tubular fabric.

A repulsive force 6 was measured by using compression rate and compressive elastic modulus measuring device SE-15 manufactured by INTEC CO., LTD., attaching a 10 $cm^2$ compression table 4 of a sample retaining ring stand and a 5 $cm^2$ gauge head 3 to the device, putting a sample, or a processed tubular fabric 2 on the compression table 4, setting the gauge head at 0 in the position where the gauge head was brought into contact with an upper part of the sample to the extent not to deform the shape of the tubular fabric, and then compressing the sample in an arrow-5 direction by the distance one-half the diameter of the sample.

(6) Weave Density of Cut-Open Tubular Fabric

The weave density was measured in compliance with JIS L 1096: 2010 8.6.1.

A sample obtained by cutting open the tubular fabric was put on a flat table, unnatural wrinkles and tension were removed, the number of warp yarns and weft yarns in a length of 0.5 cm was counted at five different locations, and the average value of each of the warp yarn and the weft yarn was calculated and converted to the number of yarns per 2.54 cm.

(7) Fracture Elongation

The fracture elongation was measured under the constant-rate-of-elongation conditions specified in the normal-state test of JIS L 1013: 2010 8.5.1. A sample was measured using "TENSILON" UCT-100 manufactured by ORIENTEC CORPORATION, at a holding interval of 25 cm and a tensile speed of 30 cm/min.

(8) Gauge-Line Distance L1 Under Compression and Gauge-Line Distance L2 Under Elongation of Tubular Fabric First, the maximum value of the outer diameter of the fabric (the outer-diameter maximum part of the tubular fabric measured without application of a stress to the tubular fabric) is determined by the above (4).

Figure 4:
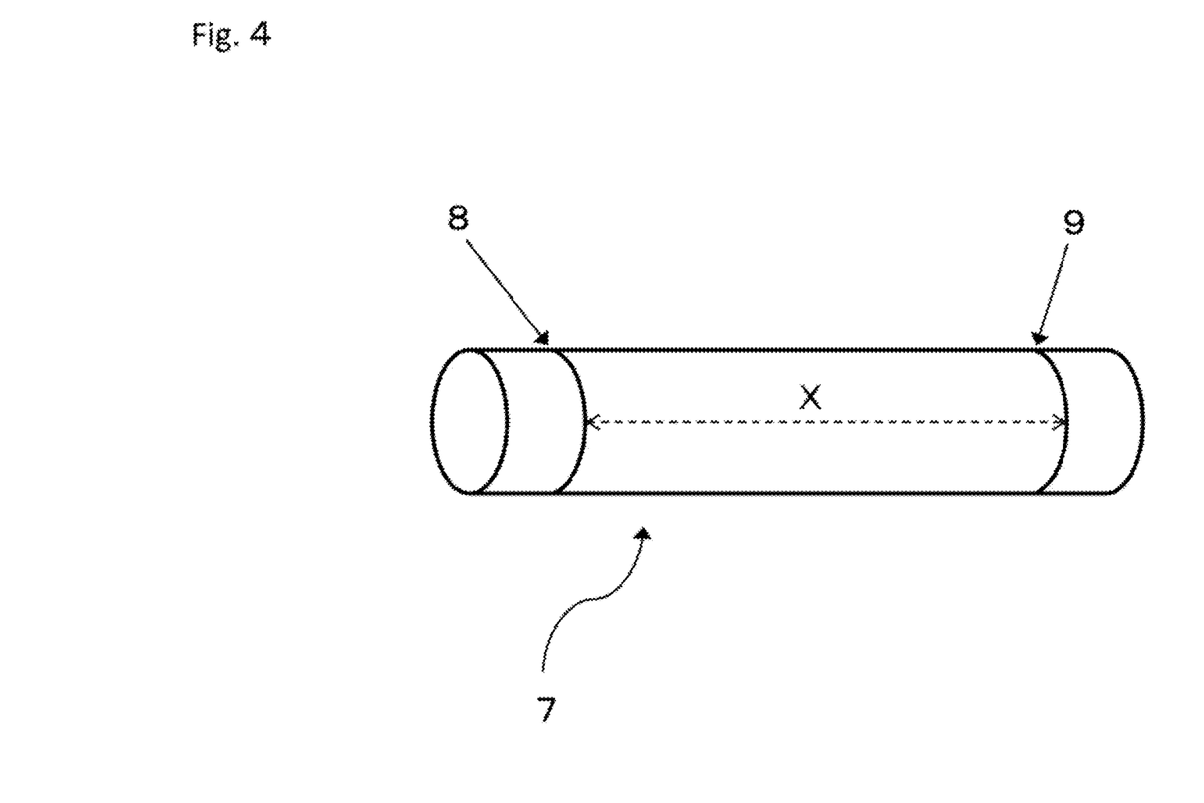
FIG. 4 is an explanatory diagram for drawing gauge lines on the tubular fabric.

Next, FIG. 4 is an explanatory diagram for drawing gauge lines on the tubular fabric. As shown in FIG. 4, a first gauge line 8 is drawn on the outer circumference of a tubular fabric 7 at a position 5 mm away from one edge of the tubular fabric. A second gauge line 9 is drawn on the outer circumference of the tubular fabric, with a distance X five times the maximum value of the outer diameter of the tubular fabric from the first gauge line. The tubular fabric 7 is cut along the diameter at a position 5 mm away from the second gauge line.

Figure 5:
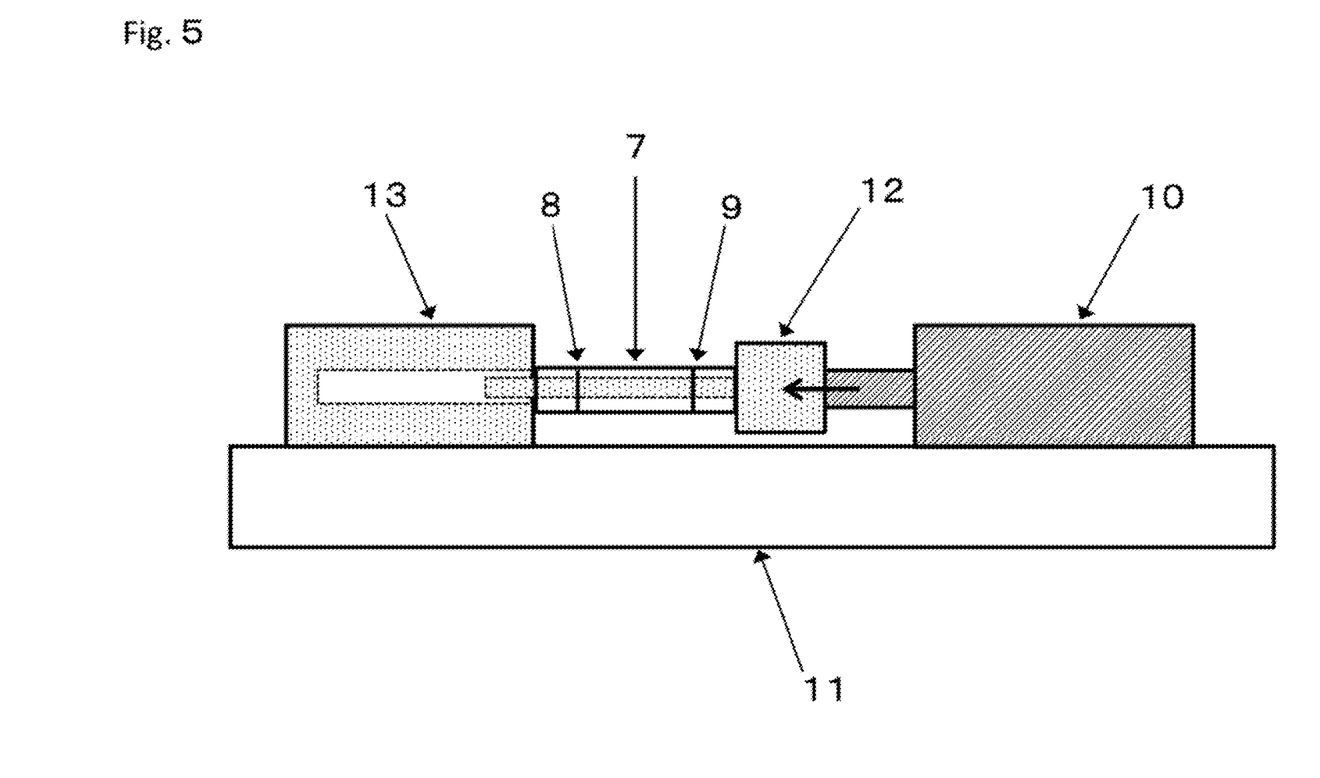
FIG. 5 is a conceptual diagram of a device for measuring the gauge-line distance under compression of the tubular fabric.

FIG. 5 is a conceptual diagram of a device for measuring the gauge-line distance under compression of the tubular fabric. As shown in FIG. 5, the device includes HANDY DIGITAL FORCE GAUGE HF-1 ((rated capacity: 10 N) manufactured by Japan Instrumentation System Co., Ltd.) that serves as a force gauge 10 and is fitted on a platform 11, a core rod portion-equipped compression chuck jig 12 attached to the force gauge 10, and a compression receiving jig 13 having a hole into which the core rod portion is insertable and being attached to the platform 11.

Then, the tubular fabric 7 was set in the device by inserting the core rod portion of the compression chuck jig 12 into the tubular fabric 7, and the gauge-line distance L1 under compression (gauge-line distance under compression) at a stress of 0.01 cN/dtex in the warp direction was measured with a caliper.

Figure 6:
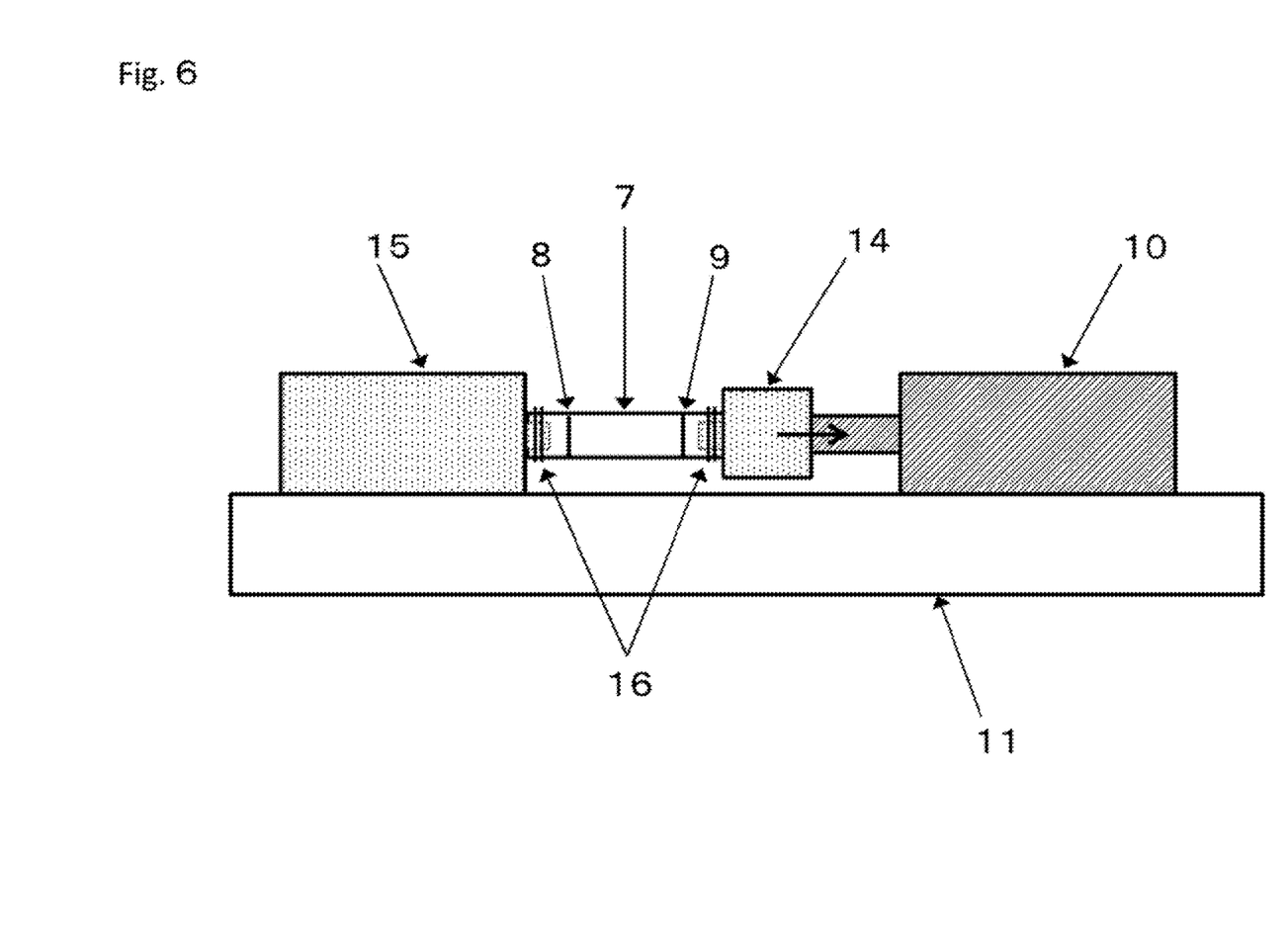
FIG. 6 is a conceptual diagram of a device for measuring the gauge-line distance under elongation of the tubular fabric.

Here, the core rod portion of the compression chuck jig 12 that is inserted into the tubular fabric 7 has a diameter of the inner-diameter minimum part of the tubular fabric 7 −0.1 mm (±0.03 mm), and the hole of the compression receiving jig 13 has the same diameter as the inner-diameter minimum part of the tubular fabric. Here, the same diameter does not have to be strictly the same diameter, but a difference of about ±0.03 mm is to be regarded as the same diameter. FIG. 6 is a conceptual diagram of a device for measuring the gauge-line distance under elongation of the tubular fabric. As shown in FIG. 6, the device includes HANDY DIGITAL FORCE GAUGE HF-1 ((rated capacity: 10 N) manufactured by Japan Instrumentation System Co., Ltd.) that serves as a force gauge 10 and is fitted on a platform 11, an elongation chuck jig 14 attached to the force gauge 10, and an elongation receiving jig 15 attached to the platform 11. The tubular fabric 7 was fixed at its outer sides of the gauge lines with fixing cords 16, and the gauge-line distance L2 under elongation (gauge-line distance under elongation) at a stress of 0.01 cN/dtex in the warp direction was measured with a caliper.

The measurement was performed five times with different samples, and the tubular fabric was evaluated by the average of the measured values.

The stress was calculated by the following equation.

$$\text{Stress }(cN)=0.01\times\text{warp-yarn fineness}\times\text{number of warp yarns}$$

Example 1

In the weaving step, the following warp yarns (the warp yarn A and the warp yarn B) and weft yarns (the weft yarn C and the weft yarn D) were used.

Warp yarn A (sea-island composite fiber): Polyethylene terephthalate fiber, 66 dtex, 9 filaments (after sea removal treatment: 52.8 dtex, 630 filaments)

Warp yarn B (soluble yarn): Easily alkali-solution polyester fiber containing copolymerized 5-sodium-sulfoisophthalic acid, 84 dtex, 24 filaments Weft yarn C (inner layer) (sea-island composite fiber): Polyethylene terephthalate fiber, 66 dtex, 9 filaments (after sea removal treatment: 52.8 dtex, 630 filaments)

Weft yarn D (outer layer): Polyethylene terephthalate fiber, 44 dtex, monofilament When the weft insertion was performed in the weaving, with the cloth-fell-end shuttle set as the weft yarn C and the beam-end shuttle set as the weft yarn D, a tubular fabric was woven while the positions of the front and back shuttles were switched in the weft insertion that causes exposure of the weft yarn C to the outside of the weft yarn D. A tubular fabric having an inner diameter of 3.3 mm was woven at a tension of the warp yarn B of 0.9 cN/dtex and a tension of the warp yarn A of 0.1 cN/dtex, to have a weave density measured by cutting open the post-processed tubular fabric of 136 yarns/inch (2.54 cm) for the warp yarn A, 120 yarns/inch (2.54 cm) for the weft yarn C, and 120 yarns/inch (2.54 cm) for the weft yarn D. The warp yarns A and B were placed at a ratio of the three warp yarns A to the one warp yarn B. The warp yarn B was placed between the weft yarn C positioned in the inner layer and the weft yarn D positioned in the outer layer.

Next, post processing was performed by the following steps.

(a) Hot Water Washing

The treatment conditions were a temperature of 98° C. and a time of 20 minutes.

(b) Pre-Heat Setting

A round rod having an outer diameter of 3.0 mm was inserted into the tubular fabric, and the tubular fabric was fixed at both ends with a wire and heat-treated. The treatment conditions were a temperature of 180° C. and a time of 5 minutes. The material for the round rod was SUS.

(c) Sea Removal Treatment

The warp yarn A and the weft yarn C were subjected to a sea removal treatment, and the warp yarn B was removed by dissolution.

(c-1) Acid Treatment

Maleic acid was used as an acid. The treatment conditions were a concentration of 0.2% by mass, a temperature of 130° C., and a time of 30 minutes.

(c-2) Alkali Treatment

Sodium hydroxide was used as an alkali. The treatment conditions were a concentration of 1.0% by mass, a temperature of 80° C., and a time of 90 minutes.

(d) Heat Setting (First Time)

A round rod having an outer diameter of 3.3 mm was inserted into the tubular fabric, and the tubular fabric was fixed at both ends with a wire or the like while maximally compressed in the warp direction so as not to allow wrinkles on the tubular fabric, and was heat-treated. The treatment conditions were a temperature of 180° C. and a time of 5 minutes. The material for the round rod was SUS.

(e) Heat Setting (Second Time)

A round rod having an outer diameter of 3.3 mm was inserted into the tubular fabric, and the tubular fabric was fixed at both ends with a wire or the like while elongated by 30% in the warp direction, and was heat-treated. The treatment conditions were a temperature of 170° C. and a time of 5 minutes. The material for the round rod was SUS.

Table 1 shows the properties of the resultant tubular fabric.

The resultant tubular fabric had good operability when manually flexed, and had excellent stretchability, softness, repulsive property, and shape-retaining ability. The tubular fabric had no accordion structure. No weft yarn C was exposed to the outer surface of the tubular fabric. When sewn with each other, the tubular fabrics had the same property of puncture in any location along the outer circumference of the tubular fabrics and had an almost true circle as the section cut along the diameter of the tubular fabrics to allow much easier sewing than of the tubular fabric obtained in Comparative Example 1 described later.

Example 2

A tubular fabric was obtained similarly to Example 1 except that the inner diameter of the tubular fabric was set at 4.0 mm and the second heat setting was not performed.

The resultant tubular fabric had good operability when manually flexed, and had excellent stretchability, softness, repulsive property, and shape-retaining ability. No weft yarn C was exposed to the outer surface of the tubular fabric. When sewn with each other, the tubular fabrics had the same property of puncture in any location along the outer circumference of the tubular fabrics and had an almost true circle as the section cut along the diameter of the tubular fabrics to allow much easier sewing than of the tubular fabric obtained in Comparative Example 2 described later.

Example 3

A tubular fabric was obtained similarly to Example 1 except that the inner diameter of the tubular fabric was set at 5.0 mm and the second heat setting was performed at an elongation of 20%.

The resultant tubular fabric had good operability when manually flexed, and had excellent stretchability, softness, repulsive property, and shape-retaining ability. No weft yarn C was exposed to the outer surface of the tubular fabric. When sewn with each other, the tubular fabrics had the same property of puncture in any location along the outer circumference of the tubular fabrics and had an almost true circle as the section cut along the diameter of the tubular fabrics to allow much easier sewing than of the tubular fabric obtained in Comparative Example 2 described later.

Example 4

A tubular fabric was obtained similarly to Example 1 except that a tubular fabric having an inner diameter of 3.3 mm was woven, with the warp yarn A used in place of the warp yarn B (soluble yarn) of the tubular fabric and the tension of all the warp yarns set at 0.5 cN/dtex, to have a weave density measured by cutting open the post-processed tubular fabric of 130 yarns/inch (2.54 cm) for the warp yarn A, 90 yarns/inch (2.54 cm) for the weft yarn C, and 90 yarns/inch (2.54 cm) for the weft yarn D, and except that the second heat setting was not performed.

The resultant tubular fabric had an excellent repulsive property and an excellent shape-retaining ability. No weft yarn C was exposed to the outer surface of the tubular fabric. When sewn with each other, the tubular fabrics had the same property of puncture in any location along the outer circumference of the tubular fabrics and had an almost true circle as the section cut along the diameter of the tubular fabrics to allow easier sewing than of the tubular fabric obtained in Comparative Example 3 described later.

Comparative Example 1

A tubular fabric was obtained similarly to Example 1 except that the tubular fabric was woven without switching the positions of the cloth-fell-end shuttle, the weft yarn C and the beam-end shuttle, the weft yarn D in the weaving.

In the resultant tubular fabric, a part where the weft yarns were intersected with each other was protruded from the contour of the tubular fabric even after the heat setting was performed with the round rod inserted into the tubular fabric, and the tubular fabric had poor circularity. Also from the viewpoint of the physical properties, the tubular fabric had poor flexure at the part where the weft yarns were intersected with each other, and had a poor balance of a perpendicular repulsive property. Further, when the tubular fabrics were sewn with each other, the base materials were hard at the part where the weft yarns were intersected with each other, and had trouble being sewn with each other.

Comparative Example 2

A tubular fabric was obtained similarly to Example 2 except that the tubular fabric was woven without switching the positions of the cloth-fell-end shuttle, the weft yarn C and the beam-end shuttle, the weft yarn D in the weaving and was woven using, as the weft yarns C and D, the same type of yarn, a polyethylene terephthalate fiber, 66 dtex, 9 filaments (after sea removal treatment: 52.8 dtex, 630 filaments).

In the resultant tubular fabric, a part where the weft yarns were intersected with each other was protruded similarly to Comparative Example 1, and the part had poor flexure and a poor balance of a perpendicular repulsive property. Further, when the tubular fabrics were sewn with each other, the base materials were hard at the part where the weft yarns were intersected with each other, and had trouble being sewn with each other.

Comparative Example 3

A tubular fabric was obtained similarly to Example 4 except that the tubular fabric was woven without switching the positions of the cloth-fell-end shuttle, the weft yarn C and the beam-end shuttle, the weft yarn D in the weaving.

In the resultant tubular fabric, a part where the weft yarns were intersected with each other was protruded even after the heat setting was performed with the round rod inserted into the tubular fabric, and the part had poor flexure and a poor balance of a perpendicular repulsive property. Further, when the tubular fabrics were sewn with each other, the base materials were hard at the part where the weft yarns were intersected with each other, and had trouble being sewn with each other.

TABLE 1

| | | Example 1 | Example 2 | Example 3 | Example 4 | Comparative Example 1 | Comparative Example 2 | Comparative Example 3 |
|---|---|---|---|---|---|---|---|---|
| Type of warp yarn A | — | Polyethylene terephthalate | Polyethylene terephthalate | Polyethylene terephthalate | Polyethylene terephthalate | Polyethylene terephthalate | Polyethylene terephthalate | Polyethylene terephthalate |
| Fineness of warp yarn A | dtex | 52.8 | 52.8 | 52.8 | 52.8 | 52.8 | 52.8 | 52.8 |
| Number of filaments in warp yarn A | filaments | 630 | 630 | 630 | 630 | 630 | 630 | 630 |
| Fracture elongation of warp yarn A | % | 30.4 | 30.4 | 30.4 | 30.4 | 30.4 | 30.4 | 30.4 |
| Single-yarn diameter of warp yarn A | μmφ | 2.78 | 2.78 | 2.78 | 2.78 | 2.78 | 2.78 | 2.78 |
| Type of weft yarn C | — | Polyethylene terephthalate | Polyethylene terephthalate | Polyethylene terephthalate | Polyethylene terephthalate | Polyethylene terephthalate | Polyethylene terephthalate | Polyethylene terephthalate |
| Fineness of weft yarn C | dtex | 52.8 | 52.8 | 52.8 | 52.8 | 52.8 | 52.8 | 52.8 |
| Number of filaments in weft yarn C | filaments | 630 | 630 | 630 | 630 | 630 | 630 | 630 |
| Fracture elongation of warp yarn C | % | 30.4 | 30.4 | 30.4 | 30.4 | 30.4 | 30.4 | 30.4 |

TABLE 1-continued

|  |  | Example 1 | Example 2 | Example 3 | Example 4 | Comparative Example 1 | Comparative Example 2 | Comparative Example 3 |
|---|---|---|---|---|---|---|---|---|
| Single-yarn diameter of weft yarn C | µmφ | 2.78 | 2.78 | 2.78 | 2.78 | 2.78 | 2.78 | 2.78 |
| Type of weft yarn D | — | Polyethylene terephthalate | Polyethylene terephthalate | Polyethylene terephthalate | Polyethylene terephthalate | Polyethylene terephthalate | Polyethylene terephthalate | Polyethylene terephthalate |
| Fineness of weft yarn D | dtex | 44 | 44 | 44 | 44 | 44 | 52.8 | 44 |
| Number of filaments in weft yarn D | filaments | 1 | 1 | 1 | 1 | 1 | 630 | 1 |
| Fracture elongation of warp yarn D | % | 32.1 | 32.1 | 32.1 | 32.1 | 32.1 | 32.1 | 32.1 |
| Single-yarn diameter of weft yarn D | µmφ | 63.72 | 63.72 | 63.72 | 63.72 | 63.72 | 2.78 | 63.72 |
| Outer diameter a | mmφ | 3.77 | 4.52 | 5.48 | 3.92 | 4.12 | 4.91 | 4.42 |
| Outer diameter b | mmφ | 3.73 | 4.42 | 5.31 | 3.82 | 3.32 | 3.84 | 3.53 |
| Circularity c = a/b | — | 1.01 | 1.02 | 1.03 | 1.03 | 1.24 | 1.28 | 1.25 |
| Repulsive force Fa | cN | 49.4 | 48.4 | 47.3 | 51.2 | 53.7 | 29.4 | 55.9 |
| Repulsive force Fb | cN | 47.8 | 47.6 | 46.9 | 49.8 | 42.8 | 24.1 | 41.6 |
| Repulsive ratio Fc = Fa/Fb | — | 1.03 | 1.02 | 1.01 | 1.03 | 1.25 | 1.22 | 1.34 |
| Gauge-line distance | mm | 18.9 | 22.6 | 27.4 | 19.6 | 20.6 | 24.6 | 22.1 |
| Gauge-line distance under compression (L1) | mm | 16.3 | 21.7 | 25.6 | 19.5 | 19.2 | 22.4 | 22.0 |
| Gauge-line distance under elongation (L2) | mm | 20.8 | 26.8 | 31.0 | 19.7 | 21.3 | 25.9 | 22.2 |
| (L2 − L1)/L1 | — | 0.28 | 0.24 | 0.21 | 0.01 | 0.11 | 0.16 | 0.01 |

A tubular fabric of the present invention is suitably usable as an artificial blood vessel, but the application range of the tubular fabric is not limited to the artificial blood vessel.

DESCRIPTION OF REFERENCE SIGNS

1: Tubular fabric (gray fabric) in weaving
2: Processed tubular fabric
3: Gauge head
4: Compression table
5: Arrow
6: Repulsive force
7: Tubular fabric
8: First gauge line
9: Second gauge line
10: Force gauge
11: Platform
12: Compression chuck jig
13: Compression receiving jig
14: Elongation chuck jig
15: Elongation receiving jig
16: Fixing code
A: Fabric width
X: Gauge-line distance five times maximum value of outer diameter of fabric
a: Outer diameter of processed base material (location corresponding to fabric width A in gray fabric)
b: Outer diameter of processed base material (fabric thickness in gray fabric)

The invention claimed is:
1. A tubular fabric comprising:
a wall part that is woven by interlacing a warp yarn and a weft yarn and has a double weave structure in each of an inner layer and an outer layer, wherein a weft yarn in the outer layer and a weft yarn in the inner layer are not intersected with each other,
wherein the tubular fabric is a quadruple fabric having a quadruple weave structure,
wherein the quadruple fabric has a first layer, a second layer, a third layer and a fourth layer,
wherein the outer layer of the wall part is formed of the first layer and the fourth layer,
wherein the inner layer of the wall part is formed of the second layer and the third layer, and
wherein the quadruple fabric has no connection point between the second layer and the third layer, and has a hollow space between the second layer and the third layer.

2. The tubular fabric according to claim 1, having a circularity c of 0.8 or more and 1.2 or less, wherein
the circularity c is represented by a following equation 1 of an outer diameter b perpendicular to an outer diameter a with respect to the outer diameter a, and
the outer diameter a is obtained by measuring a location corresponding to a fabric width A in weaving of the tubular fabric:

$$\text{Circularity } c = a/b \qquad \text{(equation 1)}.$$

3. The tubular fabric according to claim 1, having a repulsive ratio Fc of 0.8 or more and 1.2 or less, wherein
the repulsive ratio Fc is represented by a following equation 2 of a repulsive force Fb under compression along the outer diameter b of the tubular fabric by a distance one-half the outer diameter b with respect to a repulsive force Fa under compression along the outer diameter a of the tubular fabric by a distance one-half the outer diameter a:

$$\text{Repulsive ratio } Fc = Fa/Fb \qquad \text{(equation 2)}.$$

4. The tubular fabric according to claim 1, satisfying a following equation 3:

$$(L2-L1)/L1 \geq 0.1 \qquad \text{(equation 3)},$$

wherein
L1 is a gauge-line distance between gauge lines that is obtained under compression in a warp direction of the tubular fabric at a stress of 0.01 cN/dtex, the gauge lines being drawn on an outer circumference of the tubular fabric, with a distance five times a maximum value of an outer diameter of the tubular fabric measured without application of a stress to the tubular fabric; and L2 is a gauge-line distance under elongation in the warp direction at a stress of 0.01 cN/dtex.

5. The tubular fabric according to claim 1, comprising no accordion structure.

6. The tubular fabric according to claim 1, wherein the warp yarn and the weft yarn used in the tubular fabric are synthetic fibers.

7. The tubular fabric according to claim 1, wherein the synthetic fibers used as the warp yarn and/or the weft yarn are polyester having a fracture elongation of 70% or less.

8. The tubular fabric according to claim 1, wherein a synthetic fiber exposed to an inner surface constituting the tubular fabric is a multifilament whose single-yarn diameters are partially or entirely 5 μm or less.

9. The tubular fabric according to claim 1, wherein synthetic fibers in the outer layer constituting the tubular fabric are partially or entirely monofilaments having a diameter of 20 μm or more.

10. A medical base material comprising the tubular fabric according to claim 1.

11. The tubular fabric according to claim 1, wherein the tubular fabric has an inner diameter of 10 mm or less.

* * * * *